United States Patent [19]

Meilland

[11] Patent Number: Plant 5,864

[45] Date of Patent: Jan. 27, 1987

[54] ROSE PLANT—MEIKRUZA VARIETY

[75] Inventor: Marie-Louise Meilland, Antibes, France

[73] Assignee: The Conard-Pyle Company, West Grove, Pa.

[21] Appl. No.: 659,942

[22] Filed: Oct. 11, 1984

[30] Foreign Application Priority Data

Oct. 12, 1983 [FR] France ..... 4212

[51] Int. Cl.[4] ..... A01H 5/00

[52] U.S. Cl. ..... Plt./15

[58] Field of Search ..... Plt./14–15

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided having double blossoms which are of an attractive pale yellow coloration which often is very lightly suffused with a light salmon pink coloration. The new variety is well adapted for the production of long-lasting cut flowers on an abundant basis while being grown under greenhouse conditions. The new variety also exhibits excellent vigor and disease resistance.

16 Drawing Figures

SUMMARY OF THE INVENTION

The new variety of Hybrid Tea rose plant of the present invention was created by artificial pollination wherein two parents were crossed which previously had been studied in the hope that they would contribute the desired characteristics. The seed parent resulted from the artificial pollination of the Meialfi variety (non-patented) by the product of the artificial pollination of the Meger and Meban varieties (each non-patented). The pollen parent of the new variety was created by first crossing the Show Girl variety (U.S. Plant Pat. No. 646) and the Meialto variety (non-patented) to produce a seed parent which was subsequently crossed by the product of the Meialto variety (non-patented) and the Tropicana variety (U.S. Plant Pat. No. 1,969). The parentage of the new variety can be summarized as follows:

[MEIALFI × (MEGER × MEBAN)]
×
[(SHOW GIRL × MEIALTO) ×
(MEIALTO × TROPICANA)].

The seeds resulting from the above pollination were sown and 60 plantlets were obtained which were physically and biologically different from each other. Selective study resulted in the identification of a single plant of the new variety. The desirable qualities of the new variety have been confirmed through extensive testing, and the importance of the new variety has been firmly established.

It was found that the new variety of Hybrid Tea rose plant of the present invention possesses the following combination of characteristics:

(a) from a physical point of view, the plant has a deep green adult wood, an upright growth habit, and forms attractive pale yellow blossoms of long duration which often are very lightly suffused with a light salmon pink coloration and comprise consistent petals; and (b) from a biological point of view, the plant has vigorous vegetation, flowers abundantly, and exhibits good disease resistance.

The new variety meets the needs of the horticultural industry for all usages. It has been found, however, that the new variety particularly is well suited for growing in greenhouses where it forces well to produce quality cut flowers.

The blossoms of the new variety have been found to be long-lasting, and the petals detach clearly. Both the buds and the open flowers exhibit the unique coloration described herein. However, the very light salmon pink suffusion which frequently is observed tends to occur primarily when cool and/or relatively dark growing conditions are encountered (e.g., during the springtime) and then tends to be present primarily on newly opened blossoms rather than on the fully opened blossoms immediately prior to petal drop which often tend to be virtually white in coloration. The relative whiteness of the fully opened blossoms immediately prior to petal drop tends to intensify with increasing amounts of sunshine.

The new variety has been found to undergo asexual propagation by a number of routes, including budding and grafting. The characteristics of the new variety have been found to be strictly transmissible by such asexual propagation from one generation to another.

The new variety has been named the Meikruza variety.

BRIEF DESCRIPTION OF THE PHOTOGRAPH

The accompanying photograph shows as nearly true as it is reasonably possible to make the same in a color illustration of this character, typical specimens of plant parts of the new variety when observed during April. The rose plants of the new variety described herein were grown at Cap d'Antibes, France, in a greenhouse and were grafted on *Rosa indica* rootstock.

FIG. 2 illustrates a specimen of a flowering bud before the opening of the sepals;

Figures 1, 3, 4, 5, 6, 7, 8, 9, 10, 11, 12, 14, 16:
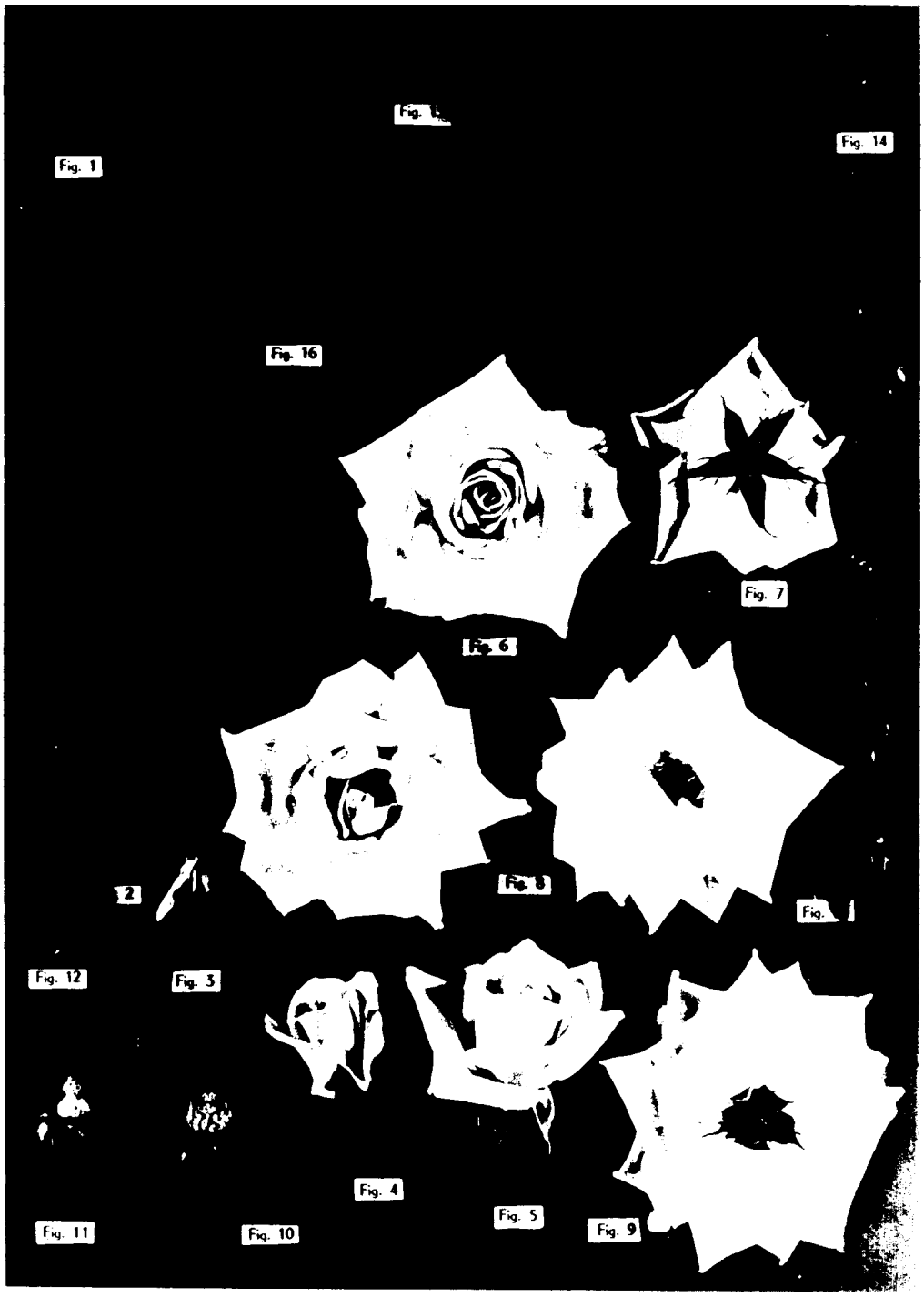
FIG. 1 illustrates a specimen of a young shoot.
FIG. 3 illustrates a specimen of a flowering bud at the opening of the sepals.
FIG. 4 illustrates a specimen of a flowering bud at the opening of the petals.
FIG. 5 illustrates a specimen of a flower at the beginning of opening.
FIG. 6 illustrates a specimen of a flower in the course of opening—plan view—obverse.
FIG. 7 illustrates a specimen of a flower in the course of opening—plan view—reverse.
FIG. 8 illustrates two specimens of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a receptacle showing the arrangement of the pistils (stamens removed)
FIG. 12 illustrates a specimen of a young flowering stem.

*Number of flowers.*—Generally one per stem.

*Peduncle.*—Straight, rigid, and smooth; its length is approximately 8 cm. on average.

*Sepals.*—Upper Surface: tomentose, greenish in coloration. Under Surface: clear green in coloration, often bearing glandular appendages on the edges.

*Buds.*—Shape: conical at the opening of the sepals, then cylindrical at the opening of the petals. Length: approximately 3.5 cm. on average. Size: medium. Color (When Opening): Upper Surface: light canary yellow (Yellow Group 9D) lightly